(12) United States Patent
Jungkamp et al.

(10) Patent No.: US 8,278,474 B2
(45) Date of Patent: *Oct. 2, 2012

(54) METHOD FOR THE SEPARATION OF PENTENENITRILE ISOMERS

(75) Inventors: Tim Jungkamp, Kapellen (BE); Robert Baumann, Mannheim (DE); Michael Bartsch, Neustadt (DE); Gerd Haderlein, Grünstadt (DE); Hermann Luyken, Ludwigshafen (DE); Jens Scheidel, Hirschberg (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

This patent is subject to a terminal disclaimer.

(21) Appl. No.: 13/047,212

(22) Filed: Mar. 14, 2011

(65) Prior Publication Data

US 2011/0166377 A1    Jul. 7, 2011

Related U.S. Application Data

(63) Continuation of application No. 10/586,452, filed as application No. PCT/EP2005/000726 on Jan. 26, 2005, now abandoned.

(30) Foreign Application Priority Data

Jan. 29, 2004    (DE) .......................... 10 2004 004 721

(51) Int. Cl.
    *C07C 253/34*    (2006.01)

(52) U.S. Cl. ...................................................... 558/465
(58) Field of Classification Search .................. 558/465
    See application file for complete search history.

(56) References Cited

U.S. PATENT DOCUMENTS

| | | |
|---|---|---|
| 3,356,746 A | 12/1967 | Cramer et al. |
| 3,526,654 A | 9/1970 | Hildebrand |
| 3,564,040 A | 2/1971 | Downing et al. |
| 3,852,325 A | 12/1974 | King |
| 3,852,327 A | 12/1974 | Druliner et al. |
| 3,865,865 A | 2/1975 | Musser et al. |
| 6,242,633 B1 | 6/2001 | Fischer et al. |
| 6,852,199 B2 | 2/2005 | Jungkamp et al. |
| 7,541,486 B2 * | 6/2009 | Scheidel et al. ............. 558/465 |
| 2002/0039221 A1 | 4/2002 | Shiraishi et al. |

FOREIGN PATENT DOCUMENTS

| | | |
|---|---|---|
| DE | 10049265 A1 | 4/2002 |
| EP | 0 274 401 A1 | 7/1988 |
| WO | WO 99/07671 A1 | 2/1999 |
| WO | WO-02/26698 A1 | 4/2002 |

OTHER PUBLICATIONS

Translation of PCT International Preliminary Report on Patentability, International Patent Application No. PCT/EP2005/000781.

* cited by examiner

*Primary Examiner* — Joseph Kosack
(74) *Attorney, Agent, or Firm* — Connolly Bove Lodge & Hutz LLP

(57) ABSTRACT

A process is described for separating mixtures of isomeric pentenenitriles, in which at least one isomer is removed from the mixture, wherein the separation of the substance mixtures of isomeric pentenenitriles is effected distillatively under reduced pressure.

14 Claims, No Drawings

METHOD FOR THE SEPARATION OF PENTENENITRILE ISOMERS

CROSS REFERENCE TO RELATED APPLICATIONS

This application is a Continuation of U.S. application Ser. No. 10/586,452, filed Jul. 18, 2006. U.S. application Ser. No. 10/586,452 is a National Phase of PCT/EP2005/000726, filed Jan. 26, 2005, which claims priority to German application 10 2004 004 721.9, filed Jan. 29, 2004.

The present invention relates to a process for preparing mixtures of isomeric pentenenitriles.

Adiponitrile, an important intermediate in nylon production, is prepared by double hydrocyanation of 1,3-butadiene. In a first hydrocyanation stage, 1,3-butadiene is reacted with hydrogen cyanide in the presence of nickel (0) which is stabilized with phosphorus ligands to give 3-pentenenitrile. Secondary components of this first hydrocyanation are substantially 2-methyl-3-butenenitrile, 2-pentenenitriles, 2-methyl-2-butenenitriles, $C_9$ nitriles, methylglutaronitrile and 4-vinylcyclohexene. In a second hydrocyanation, 3-pentenenitrile is subsequently reacted with hydrogen cyanide to give adiponitrile, likewise over a nickel catalyst, but with addition of a Lewis acid. In this second hydrocyanation too, a mixture of the reactant and product nitriles and also the abovementioned secondary components is obtained.

The complex mixtures occurring in these two reactions have to be separated from one another to carry out an economically attractive process for preparing adiponitrile. From the existing processes for preparing adiponitrile by hydrocyanating 1,3-butadiene and subsequently reacting the 3-pentenenitrile resulting therefrom with a further molecule of hydrogen cyanide, it is unknown how the complex mixtures are separated, especially with regard to the separation of pentenenitrile isomers.

As described in DE 100 49 265, the distillative separation of pentenenitrile isomers presents considerable problems, since the relative volatility α of the pentenenitrile isomers at atmospheric pressure is in the range from 1.0 to 2.0 and, for a series of isomer pairs, is in the range from 1.0 to 1.5. The relative volatility a refers to the quotient of the vapor pressures of two substances, the vapor pressure of the substance having the higher vapor pressure being taken in the numerator of the quotient.

| Pentenenitrile isomer pair | Relative volatility at atmospheric pressure |
|---|---|
| 2-Methyl-3-butenenitrile/trans-3-pentenenitrile | 1.72 |
| cis-2-Pentenenitrile/trans-3-pentenenitrile | 1.55 |
| (E)-2-Methyl-2-butenenitrile/trans-3-pentenenitrile | 1.19 |
| 2-Methyl-3-butenenitrile/(Z)-2-methyl-2-butenenitrile | 1.12 |

Although the distillative separation of the species mentioned can be realized, since the relative volatility at atmospheric pressure is higher than 1.0; it leads in practice to considerable technical complexity and energy consumption.

To circumvent a separation of trans-3-pentenenitrile and trans-2-pentenenitrile, it is proposed, for example in U.S. Pat. No. 3,526,654, U.S. Pat. No. 3,564,040, U.S. Pat. No. 3,852,325 and U.S. Pat. No. 3,852,327 to convert the pentenenitrile isomers which are difficult to remove by distillation catalytically to those which can easily be removed by distillation.

A disadvantage is that the catalytic isomerization leads to losses of products of value as a result of formation of undesired isomers or oligomers.

To circumvent a separation of (Z)-2-methyl-2-butenenitrile and 2-methyl-3-butenenitrile, and also trans-2-pentenenitrile and trans-3-pentenenitrile, U.S. Pat. No. 3,865,865 proposes treating the nitrile mixture with aqueous sulfite solution, in each case to obtain an aqueous phase comprising the particular bisulfite adducts of the conjugated nitriles (Z)-2-methyl-2-butenenitrile or trans-2-pentenenitrile, and an organic phase depleted in these nitriles. A disadvantage in this process is that the resulting organic phase first has to be freed completely of water before further use in hydrocyanation reactions using nickel(0) catalysts with phosphorus(III) ligands, since the phosphorus(III) ligands are otherwise irreversibly hydrolyzed and thus deactivated. A further disadvantage in this process is that the resulting bisulfite adducts can only be dissociated for the purpose of further using the conjugated nitriles, as described in U.S. Pat. No. 3,865,865, only under drastic conditions and only with moderate yield.

To improve the separability, DE 100 49 265 proposes increasing the removability by extractive distillation by adding liquid diluents. This process too has the disadvantage that the resulting nitrile streams, in further processing, first have to be freed completely of liquid diluent, especially water.

Accordingly, it is an object of the present invention to provide a process which enables, in a technically simple and economically viable manner, the distillative separation of pentenenitrile isomers which have a relative volatility α in the range from 1.0 to 2.0 at atmospheric pressure.

According to the invention, the object is achieved by a process for separating mixtures of isomeric pentenenitriles, in which at least one isomer is depleted from the mixture.

In the process according to the invention, the separation of the mixtures of isomeric pentenenitriles is effected distillatively under reduced pressure.

In the process according to the invention, preference is given to separating at least two different isomers.

The process according to the invention is suitable preferentially for mixtures which are selected from the group consisting of mixtures comprising 2-methyl-3-butenenitrile and 3-pentenenitrile, mixtures comprising 2-methyl-3-butenenitrile and (Z)-2-methyl-2-butenenitrile, mixtures comprising cis-2-pentenenitrile and 3-pentenenitrile and mixtures comprising (E)-2-methyl-2-butenenitrile and 3-pentenenitrile.

In the context of the present invention, the term 3-pentenenitrile refers to trans-3-pentenenitrile or mixtures which comprise trans-3-pentenenitrile, with or without cis-3-pentenenitrile and 4-pentenenitrile.

The hydrocyanation of butadiene to 3-pentenenitrile and mixtures thereof with 2-methyl-3-butenenitrile are carried out in the presence of a nickel(0) catalyst.

The Ni(0) catalysts are complexes, which contain phosphorus ligands and/or free phosphorus ligands preferably homogeneously dissolved nickel(0) complexes.

The phosphorus ligands of the nickel(0) complexes and the free phosphorus ligands are preferably selected from mono- or bidentate phosphines, phosphites, phosphinites and phosphonites.

These phosphorus ligands preferably have the formula I

$$P(X^1R^1)(X^2R^2)(X^3R^3) \quad (I)$$

In the context of the present invention, compound I is a single compound or a mixture of different compounds of the aforementioned formula.

According to the invention, $X^1, X^2, X^3$ each independently are oxygen or a single bond. When all of the $X^1, X^2$ and $X^3$ groups are single bonds, compound I is a phosphine of the formula $P(R^1R^2R^3)$ with the definitions of $R^1, R^2$ and $R^3$ specified in this description.

When two of the $X^1, X^2$ and $X^3$ groups are single bonds and one is oxygen, compound I is a phosphinite of the formula $P(OR^1)(R^2)(R^3)$ or $P(R^1)(OR^2)(R^3)$ or $P(R^1)(R^2)(OR^3)$ with the definitions of $R^1, R^2$ and $R^3$ specified hereinbelow.

When one of the $X^1, X^2$ and $X^3$ groups is a single bond and two are oxygen, compound I is a phosphonite of the formula $P(OR^1)(OR^2)(R^3)$ or $P(R^1)(OR^2)(OR^3)$ or $P(OR^1)(R^2)(OR^3)$ with the definitions of $R^1, R^2$ and $R^3$ specified in this description.

In a preferred embodiment, all $X^1, X^2$ and $X^3$ groups should be oxygen, so that compound I is advantageously a phosphite of the formula $P(OR^1)(OR^2)(OR^3)$ with the definitions of $R^1, R^2$ and $R^3$ specified hereinbelow.

According to the invention, $R^1, R^2, R^3$ are each independently identical or different organic radicals. $R^1, R^2$ and $R^3$ are each independently alkyl radicals preferably having from 1 to 10 carbon atoms, such as methyl, ethyl, n-propyl, i-propyl, n-butyl, i-butyl, s-butyl, t-butyl, aryl groups such as phenyl, o-tolyl, m-tolyl, p-tolyl, 1-naphthyl, 2-naphthyl, or hydrocarbyl, preferably having from 1 to 20 carbon atoms, such as 1,1'-biphenol, 1,1'-binaphthol. The $R^1, R^2$ and $R^3$ groups may be bonded together directly, i.e. not solely via the central phosphorus atom. Preference is given to the $R^1, R^2$ and $R^3$ groups not being bonded together directly.

In a preferred embodiment, $R^1, R^2$ and $R^3$ are radicals selected from the group consisting of phenyl, o-tolyl, m-tolyl and p-tolyl. In a particularly preferred embodiment, a maximum of two of the $R^1, R^2$ and $R^3$ groups should be phenyl groups.

In another preferred embodiment, a maximum of two of the $R^1, R^2$ and $R^3$ groups should be o-tolyl groups.

Particularly preferred compounds I which may be used are those of the formula I a

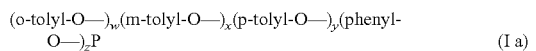
$$(o\text{-tolyl-O}—)_w(m\text{-tolyl-O}—)_x(p\text{-tolyl-O}—)_y(\text{phenyl-O}—)_zP \quad (I\,a)$$

where w, x, y, z are each a natural number, and the following conditions apply: w+x+y+z=3 and w, z≦2.

Such compounds I a are, for example, (p-tolyl-O—)(phenyl-O—)₂P, (m-tolyl-O—)(phenyl-O—)₂P, (o-tolyl-O—)(phenyl-O—)₂P, (p-tolyl-O—)₂(phenyl-O—)P, (m-tolyl-O—)₂(phenyl-O—)P, (o-tolyl-O—)₂(phenyl-O—)P, (m-tolyl-O—)(p-tolyl-O—)(phenyl-O—)P, (o-tolyl-O—)(p-tolyl-O—) (phenyl-O—)P, (o-tolyl-O—)(m-tolyl-O—)(phenyl-O—)P, (p-tolyl-O—)₃P, (m-tolyl-O—)(p-tolyl-O—)₂P, (o-tolyl-O—)(p-tolyl-O—)₂P, (m-tolyl-O—)₂(p-tolyl-O—)P, (o-tolyl-O—)₂(p-tolyl-O—)P, (o-tolyl-O—)(m-tolyl-O—)(p-tolyl-O—)P, (m-tolyl-O—)₃P, (o-tolyl-O—)(m-tolyl-O—)₂P (o-tolyl-O—)₂(m-tolyl-O—)P or mixtures of such compounds.

Mixtures comprising (m-tolyl-O—)₃P, (m-tolyl-O—)₂(p-tolyl-O—)P(m-tolyl-O—)(p-tolyl-O—)₂P and (p-tolyl-O—)₃P may be obtained, for example, by reacting a mixture comprising m-cresol and p-cresol, in particular in a molar ratio of 2:1, as obtained in the distillative workup of crude oil, with a phosphorus trihalide, such as phosphorus trichloride.

In another, likewise preferred embodiment, the phosphorus ligands are the phosphites, described in detail in DE-A 199 53 058, of the formula I b:

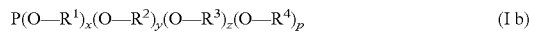
$$P(O—R^1)_x(O—R^2)_y(O—R^3)_z(O—R^4)_p \quad (I\,b)$$

where $R^1$: aromatic radical having a $C_1$-$C_{18}$-alkyl substituent in the o-position to the oxygen atom which joins the phosphorus atom to the aromatic system, or having an aromatic substituent in the o-position to the oxygen atom which joins the phosphorus atom to the aromatic system, or having a fused aromatic system in the o-position to the oxygen atom which joins the phosphorus atom to the aromatic system, $R^2$: aromatic radical having a $C_1$-$C_{18}$-alkyl substituent in the m-position to the oxygen atom which joins the phosphorus atom to the aromatic system, or having an aromatic substituent in the m-position to the oxygen atom which joins the phosphorus atom to the aromatic system, or having a fused aromatic system in the m-position to the oxygen atom which joins the phosphorus atom to the aromatic system, the aromatic radical bearing a hydrogen atom in the o-position to the oxygen atom which joins the phosphorus atom to the aromatic system, $R^3$: aromatic radical having a $C_1$-$C_{18}$-alkyl substituent in the p-position to the oxygen atom which joins the phosphorus atom to the aromatic system, or having an aromatic substituent in the p-position to the oxygen atom which joins the phosphorus atom to the aromatic system, the aromatic radical bearing a hydrogen atom in the o-position to the oxygen atom which joins the phosphorus atom to the aromatic system, $R^4$: aromatic radical which bears substituents other than those defined for $R^1, R^2$ and $R^3$ in the o-, m- and p-position to the oxygen atom which joins the phosphorus atom to the aromatic system, the aromatic radical bearing a hydrogen atom in the o-position to the oxygen atom which joins the phosphorus atom to the aromatic system, x: 1 or 2, y, z, p: each independently 0, 1 or 2, with the proviso that x+y+z+p=3.

Preferred phosphites of the formula I b can be taken from DE-A 199 53 058. The $R^1$ radical may advantageously be o-tolyl, o-ethylphenyl, o-n-propylphenyl, o-isopropyl-phenyl, o-n-butylphenyl, o-sec-butylphenyl, o-tert-butylphenyl, (o-phenyl)phenyl or 1-naphthyl groups.

Preferred $R^2$ radicals are m-tolyl, m-ethylphenyl, m-n-propylphenyl, m-isopropylphenyl, m-n-butylphenyl, m-sec-butylphenyl, m-tert-butylphenyl, (m-phenyl)phenyl or 2-naphthyl groups.

Advantageous $R^3$ radicals are p-tolyl, p-ethylphenyl, p-n-propylphenyl, p-isopropyl-phenyl, p-n-butylphenyl, p-sec-butylphenyl, p-tert-butylphenyl or (p-phenyl)phenyl groups.

The $R^4$ radical is preferably phenyl. p is preferably zero. For the indices x, y, z and p in compound I b, there are the following possibilities:

| x | y | z | p |
|---|---|---|---|
| 1 | 0 | 0 | 2 |
| 1 | 0 | 1 | 1 |
| 1 | 1 | 0 | 1 |
| 2 | 0 | 0 | 1 |

-continued

| x | y | z | p |
|---|---|---|---|
| 1 | 0 | 2 | 0 |
| 1 | 1 | 1 | 0 |
| 1 | 2 | 0 | 0 |
| 2 | 0 | 1 | 0 |
| 2 | 1 | 0 | 0 |

Preferred phosphites of the formula I b are those in which p is zero, and $R^1$, $R^2$ and $R^3$ are each independently selected from o-isopropylphenyl, m-tolyl and p-tolyl, and $R^4$ is phenyl.

Particularly preferred phosphites of the formula I b are those in which $R^1$ is the o-isopropylphenyl radical, $R^2$ is the m-tolyl radical and $R^3$ is the p-tolyl radical with the indices specified in the table above; also those in which $R^1$ is the o-tolyl radical, $R^2$ is the m-tolyl radical and $R^3$ is the p-tolyl radical with the indices specified in the table; additionally those in which $R^1$ is the 1-naphthyl radical, $R^2$ is the m-tolyl radical and $R^3$ is the p-tolyl radical with the indices specified in the table; also those in which $R^1$ is the o-tolyl radical, $R^2$ is the 2-naphthyl radical and $R^3$ is the p-tolyl radical with the indices specified in the table; and finally those in which $R^1$ is the o-isopropylphenyl radical, $R^2$ is the 2-naphthyl radical and $R^3$ is the p-tolyl radical with the indices specified in the table; and also mixtures of these phosphites.

Phosphites of the formula I b may be obtained by a) reacting a phosphorus trihalide with an alcohol selected from the group consisting of $R^1OH$, $R^2OH$, $R^3OH$ and $R^4OH$ or mixtures thereof to obtain a dihalophosphorous monoester, b) reacting the dihalophosphorous monoester mentioned with an alcohol selected from the group consisting of WOK $R^2OH$, $R^3OH$ and $R^4OH$ or mixtures thereof to obtain a monohalophosphorous diester and c) reacting the monohalophosphorous diester mentioned with an alcohol selected from the group consisting of $R^1OH$, $R^2OH$, $R^3OH$ and $R^4OH$ or mixtures thereof to obtain a phosphite of the formula I b.

The reaction may be carried out in three separate steps. Equally, two of the three steps may be combined, i.e. a) with b) or b) with c). Alternatively, all of the steps a), b) and c) may be combined together.

Suitable parameters and amounts of the alcohols selected from the group consisting of $R^1OH$, $R^2OH$, $R^3OH$ and $R^4OH$ or mixtures thereof may be determined readily by a few simple preliminary experiments.

Useful phosphorus trihalides are in principle all phosphorus trihalides, preferably those in which the halide used is Cl, Br, I, in particular Cl, and mixtures thereof. It is also possible to use mixtures of various identically or differently halogen-substituted phosphines as the phosphorus trihalide. Particular preference is given to $PCl_3$. Further details on the reaction conditions in the preparation of the phosphites I b and for the workup can be taken from DE-A 199 53 058.

The phosphites I b may also be used in the form of a mixture of different phosphites I b as a ligand. Such a mixture may be obtained, for example, in the preparation of the phosphites I b.

However, preference is given to the phosphorus ligand being multidentate, in particular bidentate. The ligand used therefore preferably has the formula II

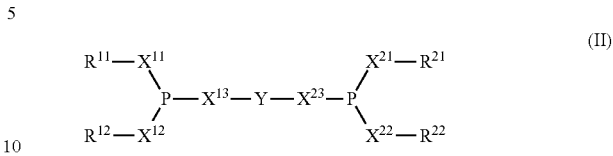

where
$X^{11}, X^{12}, X^{13}, X^{21}, X^{22}, X^{23}$ are each independently oxygen or a single bond
$R^{11}, R^{12}$ are each independently identical or different, separate or bridged organic radicals
$R^{21}, R^{22}$ are each independently identical or different, separate or bridged organic radicals,
Y is a bridging group.

In the context of the present invention, compound II is a single compound or a mixture of different compounds of the aforementioned formula.

In a preferred embodiment, $X^{11}, X^{12}, X^{13}, X^{21}, X^{22}, X^{23}$ may each be oxygen. In such a case, the bridging group Y is bonded to phosphite groups.

In another preferred embodiment, $X^{11}$ and $X^{12}$ may each be oxygen and $X^{13}$ a single bond; or $X^{11}$ and $X^{13}$ each oxygen and $X^{12}$ a single bond, so that the phosphorus atom surrounded by $X^{11}, X^{12}$ and $X^{13}$ each is the central atom of a phosphonite. In such a case, $X^{21}, X^{22}$ and $X^{23}$ may each be oxygen, or $X^{21}$ and $X^{22}$ may each be oxygen and $X^{23}$ a single bond, or $X^{21}$ and $X^{23}$ may each be oxygen and $X^{22}$ a single bond, or $X^{23}$ may be oxygen and $X^{21}$ and $X^{22}$ each a single bond, or $X^{21}$ may be oxygen and $X^{22}$ and $X^{23}$ each a single bond, or $X^{21}, X^{22}$ and $X^{23}$ may each be a single bond, so that the phosphorus atom surrounded by $X^{21}, X^{22}$ and $X^{23}$ may be the central atom of a phosphite, phosphonite, phosphinite or phosphine, preferably a phosphonite.

In another preferred embodiment, $X^{13}$ may be oxygen and $X^{11}$ and $X^{12}$ each a single bond, or $X^{11}$ may be oxygen and $X^{12}$ and $X^{13}$ each a single bond, so that the phosphorus atom surrounded by $X^{11}, X^{12}$ and $X^{13}$ is the central atom of a phosphonite. In such a case, $X^{21}, X^{22}$ and $X^{23}$ may each be oxygen, or $X^{23}$ may be oxygen and $X^{21}$ and $X^{22}$ each a single bond, or $X^{21}$ may be oxygen and $X^{22}$ and $X^{23}$ each a single bond, or $X^{21}, X^{22}$ and $X^{23}$ may each be a single bond, so that the phosphorus atom surrounded by $X^{21}, X^{22}$ and $X^{23}$ may be the central atom of a phosphite, phosphinite or phosphine, preferably a phosphinite.

In another preferred embodiment, $X^{11}, X^{12}$ and $X^{13}$ may each be a single bond, so that the phosphorus atom surrounded by $X^{11}, X^{12}$ and $X^{13}$ is the central atom of a phosphine. In such a case, $X^{21}, X^{22}$ and $X^{23}$ may each be oxygen, or $X^{21}, X^{22}$ and $X^{23}$ may each be a single bond, so that the phosphorus atom surrounded by $X^{21}, X^{22}$ and $X^{23}$ may be the central atom of a phosphite or phosphine, preferably a phosphine.

The bridging group Y is advantageously an aryl group which is substituted, for example by $C_1$-$C_4$-alkyl, halogen, such as fluorine, chlorine, bromine, halogenated alkyl, such as trifluoromethyl, aryl, such as phenyl, or is unsubstituted, preferably a group having from 6 to 20 carbon atoms in the aromatic system, in particular pyrocatechol, bis(phenol) or bis(naphthol).

The $R^{11}$ and $R^{12}$ radicals may each independently be identical or different organic radicals. Advantageous $R^{11}$ and $R^{12}$ radicals are aryl radicals, preferably those having from 6 to 10 carbon atoms, which may be unsubstituted or mono- or polysubstituted, in particular by $C_1$-$C_4$-alkyl, halogen, such as fluorine, chlorine, bromine, halogenated alkyl, such as trifluoromethyl, aryl, such as phenyl, or unsubstituted aryl groups.

The $R^{21}$ and $R^{22}$ radicals may each independently be the same or different organic radicals. Advantageous $R^{21}$ and $R^{22}$ radicals are aryl radicals, preferably those having from 6 to 10 carbon atoms, which may be unsubstituted or mono- or polysubstituted, in particular by $C_1$-$C_4$-alkyl, halogen, such as fluorine, chlorine, bromine, halogenated alkyl, such as trifluoromethyl, aryl, such as phenyl, or unsubstituted aryl groups.

The $R^{11}$ and $R^{12}$ radicals may each be separate or bridged. The $R^{21}$ and $R^{22}$ radicals may also each be separate or bridged. The $R^{11}$, $R^{12}$, $R^{21}$ and $R^{22}$ radicals may each be separate, two may be bridged and two separate, or all four may be bridged, in the manner described.

In a particularly preferred embodiment, useful compounds are those of the formula I, II, III, IV and V specified in U.S. Pat. No. 5,723,641. In a particularly preferred embodiment, useful compounds are those of the formula I, II, III, IV, V, VI and VII specified in U.S. Pat. No. 5,512,696, in particular the compounds used there in examples 1 to 31. In a particularly preferred embodiment, useful compounds are those of the formula I, II, III, IV, V, VI, VII, VIII, IX, X, XI, XII, XIII, XIV and XV specified in U.S. Pat. No. 5,821,378, in particular the compounds used there in examples 1 to 73.

In a particularly preferred embodiment, useful compounds are those of the formula I, II, III, IV, V and VI specified in U.S. Pat. No. 5,512,695, in particular the compounds used there in examples 1 to 6. In a particularly preferred embodiment, useful compounds are those of the formula I, II, III, IV, V, VI, VII, VIII, IX, X, XI, XII, XIII and XIV specified in U.S. Pat. No. 5,981,772, in particular the compounds used there in examples 1 to 66.

In a particularly preferred embodiment, useful compounds are those specified in U.S. Pat. No. 6,127,567 and the compounds used there in examples 1 to 29. In a particularly preferred embodiment, useful compounds are those of the formula I, II, III, IV, V, VI, VII, VIII, IX and X specified in U.S. Pat. No. 6,020,516, in particular the compounds used there in examples 1 to 33. In a particularly preferred embodiment, useful compounds are those specified in U.S. Pat. No. 5,959,135, and the compounds used there in examples 1 to 13.

In a particularly preferred embodiment, useful compounds are those of the formula I, II and III specified in U.S. Pat. No. 5,847,191. In a particularly preferred embodiment, useful compounds are those specified in U.S. Pat. No. 5,523,453, in particular the compounds illustrated there in formula 1, 2, 3, 4, 5, 6, 7, 8, 9, 10, 11, 12, 13, 14, 15, 16, 17, 18, 19, and 21. In a particularly preferred embodiment, useful compounds are those specified in WO 01/14392, preferably the compounds illustrated there in formula V, VI, VII, VIII, IX, X, XI, XII, XIII, XIV, XV, XVI, XVII, XXI, XXII, XXIII.

In a particularly preferred embodiment, useful compounds are those specified in WO 98/27054. In a particularly preferred embodiment, useful compounds are those specified in WO 99/13983. In a particularly preferred embodiment, useful compounds are those specified in WO 99/64155.

In a particularly preferred embodiment, useful compounds are those specified in the German patent application DE 100 380 37. In a particularly preferred embodiment, useful compounds are those specified in the German patent application DE 100 460 25. In a particularly preferred embodiment, useful compounds are those specified in the German patent application DE 101 502 85.

In a particularly preferred embodiment, useful compounds are those specified in the German patent application DE 101 502 86. In a particularly preferred embodiment, useful compounds are those specified in the German patent application DE 102 071 65. In a further particularly preferred embodiment of the present invention, useful phosphorus chelate ligands are those specified in US 2003/0100442 A1.

In a further particularly preferred embodiment of the present invention, useful phosphorus chelate ligands are those specified in the German patent application reference number DE 103 50 999.2 of Oct. 30, 2003 which has an earlier priority date but had not been published at the priority date of the present application.

The compounds I, I a, I b and II and their preparation are known per se. Phosphorus ligands used may also be mixture comprising at least two of the compounds I, I a, I b and II.

In a particularly preferred embodiment of the process according to the invention, the phosphorus ligand of the nickel(0) complex and/or the free phosphorus ligand is selected from tritolyl phosphite, bidentate phosphorus chelate ligands and the phosphites of the formula I b

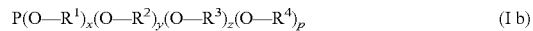

$$P(O-R^1)_x(O-R^2)_y(O-R^3)_z(O-R^4)_p \qquad (Ib)$$

where $R^1$, $R^2$ and $R^3$ are each independently selected from o-isopropylphenyl, m-tolyl and p-tolyl, $R^4$ is phenyl; x is 1 or 2, and y, z, p are each independently 0, 1 or 2 with the proviso that $x+y+z+p=3$; and mixtures thereof.

The desired products of this hydrocyanation which can be used for preparing adiponitrile are trans-3-pentenenitrile, cis-3-pentenenitrile and 4-pentenenitrile, which are referred to in the context of the present invention as 3-pentenenitrile. However, the 2-methyl-3-butenenitrile occurring in the hydrocyanation, depending on the catalyst system, in at least double-digit percentages, based on the sum of all pentenenitrile isomers formed, has to be removed before the further processing of the hydrocyanation effluent. The specification for the depletion of 2-methyl-3-butenenitrile in the 3-pentenenitrile is strict and has to be complied with because methylglutaronitrile (MGN), an undesired by-product of adiponitrile production, would form from 2-methyl-3-butenenitrile in the subsequent hydrocyanation. However, the complex apparatus and the energy requirements for the virtually complete removal of 2-methyl-3-butenenitrile from 3-pentenenitrile is very high and is determined by the relative volatility, defined as the ratio of the vapor pressures of these two substances, which is approx. 1.7 at atmospheric pressure, derived from the known standard boiling points of 416.8 K for trans-3-pentenenitrile and 396.1 K for 2-methyl-3-butenenitrile. It has been found in accordance with the invention that the relative volatility of 2-methyl-3-butenenitrile and 3-pentenenitrile increases at pressures below atmospheric pressure.

Accordingly, the process according to the invention is determined in one embodiment I for separating mixtures which comprise 2-methyl-3-butenenitrile and 3-pentenenitrile. These mixtures are preferably obtained in a reaction of 1,3-butadiene with hydrogen cyanide over a hydrocyanation catalyst, the hydrocyanation effluent typically comprising a proportion of 1,3-butadiene unconverted in the hydrocyanation which can be removed at least partly by suitable processes, and the catalyst content present in the product stream obtained in this way being removable by suitable processes. Processes of this type are described, for example, in DE-A-102 004 004 720 and DE-A-102 004 004 724. However, it is not necessarily obligatory to remove the unconverted 1,3-butadiene and the catalyst content.

The mixture which comprises 2-methyl-3-butenenitrile and 3-pentenenitrile preferably has a proportion in the mixture of from 0.1 to 99.9% by weight, more preferably from 1 to 99% by weight, in particular from 10 to 90% by weight, based in each case on the sum of the pentenenitrile isomers in the mixture. The proportion of 3-pentenenitrile in the mixture is preferably from 0.1 to 99.9% by weight, more preferably from 1 to 99% by weight, in particular from 10 to 90% by weight, based in each case on the sum of the pentenenitrile isomers in the mixture.

The separation of the mixture which comprises 2-methyl-3-butenenitrile and 3-pentenenitrile may be carried out in any suitable apparatus known to those skilled in the art. Suitable apparatus for the distillation is as described, for example, in: Kirk-Othmer, Encyclopedia of Chemical Technology, 4th Ed., Vol. 8, John Wiley & Sons, New York, 1996, page 334-348, such as sieve tray columns, bubble-cap tray columns, columns having structured packing or random packing, which may also be operated as dividing wall columns. This distillation apparatus is in each case equipped with suitable apparatus for evaporation such as falling-film evaporators, thin-film evaporators, multiphase helical tube evaporators, natural circulation evaporators or forced circulation flash evaporators, and also with apparatus for condensing the vapor stream. The distillation may be carried out in a plurality of, such as 2 or 3, apparatuses, preferably in a single apparatus. The distillation may additionally be effected in one stage in the case of a partial evaporation of the feed stream.

The number of theoretical plates in the distillation column is preferably from 0 to 100, more preferably from 1 to 60, in particular from 10 to 40. The reflux ratio, m(top draw)/–m (reflux to column) is preferably from 0.01 to 100, more preferably from 0.1 to 10, in particular from 0.2 to 5. The feed into the distillation column may be in liquid form or gaseous form. The feed into the rectification column may be into the bottom or to the top of the column. The feed is preferably to the height of the column which corresponds to from 1 to 99%, more preferably from 5 to 90%, in particular from 10 to 80%, of the total number of stages of the column, in each case counted from the bottom of the column up.

The distillation of the mixture comprising 2-methyl-3-butenenitrile and 3-pentenenitrile is preferably effected at a pressure of from 0.001 to 1 bar, more preferably from 0.01 to 0.5 bar, in particular from 0.05 to 0.2 bar. The distillation is preferably carried out in such a way that the temperature in the bottom is from 20 to 200° C., more preferably from 30 to 150° C., in particular from 50 to 100° C. The distillation is carried out in such a way that the temperature at the top is preferably from −15 to 200° C., more preferably from 0 to 100° C., in particular from 20 to 50° C. In a particularly preferred embodiment of the process according to the invention, the aforementioned temperature ranges are attained both in the bottom and at the top of the distillation apparatus.

At the top of the distillation apparatus is obtained a mixture enriched in 2-methyl-3-butenenitrile compared to the feed stream. Via the bottom of the distillation apparatus is obtained a mixture enriched in 3-pentenenitrile compared to the feed stream.

In one embodiment II, the process according to the invention relates to the separation of mixtures which comprise 2-methyl-3-butenenitrile and (Z)-2-methyl-2-butenenitrile.

As already described above, 1,3-butadiene is initially hydrocyanated to 3-pentenenitrile in a hydrocyanation process for preparing adiponitrile. A by-product obtained is 2-methyl-3-butenenitrile. As described in embodiment I of the present invention, this is preferably removed from the reaction stream before a second hydrocyanation step. The 2-methyl-3-butenenitrile removed may be isomerized to the product of value, 3-pentenenitrile, within an integrated process for hydrocyanating 1,3-butadiene in additional process steps. During this isomerization, (Z)-2-methyl-2-butenenitrile is formed as a by-product and should be removed from the 2-methyl-3-butenenitrile in the workup of the isomerization effluent in order to prevent accumulations in the process in the event of recycling of 2-methyl-3-butenenitrile in the isomerization step.

Owing to virtually equal boiling points, it is not possible to separate (Z)-2-methyl-2-butenenitrile from 2-methyl-3-butenenitrile at atmospheric pressure by distillation at an economically acceptable level of complexity and expense. The complex apparatus and the energy requirement for depleting (Z)-2-methyl-2-butenenitrile from mixtures which comprise 2-methyl-3-butenenitrile is extremely high and is determined by the relative volatility, defined as the ratio of the vapor pressures of these two substances, which is approx. 1.1 at atmospheric pressure, derived from the known standard boiling points of 392.1 K for (Z)-2-methyl-3-butenenitrile and 396.1 K for 2-methyl-3-butenenitrile. It has been found in accordance with the invention that the relative volatilities of (Z)-2-methyl-2-butenenitrile and 2-methyl-3-butenenitrile rise at pressures below atmospheric pressure, so that a removal of (Z)-2-methyl-2-butenenitrile from mixtures which comprise 2-methyl-3-butenenitrile is possible under reduced pressure at an economically acceptable level of complexity and expense.

The process according to the invention is thus also suitable preferentially for separating mixtures which comprise 2-methyl-3-butenenitrile and (Z)-2-methyl-2-butenenitrile, and stem, for example, from an isomerization of 2-methyl-3-butenenitrile.

The isomerization is preferably carried out in the presence of a system comprising
a) nickel(0),
b) a trivalent phosphorus-containing compound which complexes nickel(0) as a ligand and
c) a Lewis acid.

The nickel(0)-containing catalyst systems can be prepared by processes known per se.

The ligands used for the isomerization catalyst may be the same phosphorus ligands as for the above-described hydrocyanation.

In addition, the system may comprise a Lewis acid.

In the context of the present invention, a Lewis acid refers to a single Lewis acid, or else a mixture of a plurality of, such as two, three or four, Lewis acids.

Useful Lewis acids are inorganic or organic metal compounds in which the cation is selected from the group consisting of scandium, titanium, vanadium, chromium, manganese, iron, cobalt, copper, zinc, boron, aluminum, yttrium, zirconium, niobium, molybdenum, cadmium, rhenium and tin. Examples include $ZnBr_2$, $ZnI_2$, $ZnCl_2$, $ZnSO_4$, $CuCl_2$, $CuCl$, $Cu(O_3SCF_3)_2$, $CoCl_2$, $CoI_2$, $FeI_2$, $FeCl_3$, $FeCl_2$, $FeCl_2(THF)_2$, $TiCl_4(THF)_2$, $TiCl_4$, $TiCl_3$, $ClTi(O-i-propyl)_3$, $MnCl_2$, $ScCl_3$, $AlCl_3$, $(C_8H_{17})AlCl_2$, $(C_8H_{17})_2AlCl$, $(i-C_4H_9)_2AlCl$, $(C_6H_5)_2AlCl$, $(C_6H_5)AlCl_2$, $ReCl_5$, $ZrCl_4$, $NbCl_5$, $VCl_3$, $CrCl_2$, $MoCl_5$, $YCl_3$, $CdCl_2$, $LaCl_3$, $Er(O_3SCF_3)_3$, $Yb(O_2CCF_3)_3$, $SmCl_3$, $B(C_6H_5)_3$, $TaCl_5$, as described, for example, in U.S. Pat. No. 6,127,567, U.S. Pat. No. 6,171,996 and U.S. Pat. No. 6,380,421. Also useful are metal salts such as $ZnCl_2$, $CoI_2$ and $SnCl_2$, and organometallic compounds such as $RAlCl_2$, $R_2AlCl$, $RSnO_3SCF_3$ and $R_3B$, where R is an alkyl or aryl group, as described, for example, in U.S. Pat. No. 3,496,217, U.S. Pat. No. 3,496,218 and U.S. Pat. No. 4,774,353. According to U.S. Pat. No. 3,773,809, the promoter used may also be a metal in cationic form which is selected from the group consisting of zinc, cadmium, beryllium, aluminum, gallium, indium, thallium, titanium, zirconium, hafnium, erbium, germanium, tin, vanadium, niobium, scandium, chromium, molybdenum, tungsten, manganese, rhenium, palladium, thorium, iron and cobalt, preferably zinc, cadmium, titanium, tin, chromium, iron and cobalt, and the anionic moiety of the compound may be selected from the group consisting of halides such as fluoride, chloride, bromide and iodide, anions of lower fatty acids having from 2 to 7 carbon atoms, $HPO_3^{2-}$, $H_3PO^{2-}$, $CF_3COO^-$, $C_7H_{15}OSO_2^-$ or $SO_4^{2-}$. Further suitable promoters disclosed by U.S. Pat. No. 3,773,809 are borohydrides, organoborohydrides and boric esters of the formula $R_3B$ and $B(OR)_3$, where R is selected from the group consisting of hydrogen, aryl radicals having from 6 to 18 carbon atoms, aryl radicals substituted by alkyl groups having from 1 to 7 carbon atoms and aryl radicals substituted by cyano-substituted alkyl groups having from 1 to 7 carbon atoms, advantageously triphenylboron. Moreover, as described in U.S. Pat. No. 4,874,884, it is possible to use synergistically active combinations of Lewis acids, in order to increase the activity of the catalyst system. Suitable promoters may, for example, be selected from the group consisting of $CdCl_2$, $FeCl_2$, $ZnCl_2$, $B(C_6H_5)_3$ and $(C_6H_5)_3SnX$ where $X=CF_3SO_3$, $CH_3C_6H_4SO_3$ or $(C_6H_5)_3BCN$, and the preferred ratio specified of promoter to nickel is from about 1:16 to about 50:1.

In the context of the present invention, the term Lewis acid also includes the promoters specified in U.S. Pat. No. 3,496,217, U.S. Pat. No. 3,496,218, U.S. Pat. No. 4,774,353, U.S. Pat. No. 4,874,884, U.S. Pat. No. 6,127,567, U.S. Pat. No. 6,171,996 and U.S. Pat. No. 6,380,421.

Particularly preferred Lewis acids among those mentioned are in particular metal salts, more preferably metal halides, such as fluorides, chlorides, bromides, iodides, in particular chlorides, of which particular preference is given to zinc chloride, iron(II) chloride and iron(III) chloride.

The isomerization may be carried out in the presence of a liquid diluent, for example a hydrocarbon such as hexane, heptane, octane, cyclohexane, methylcyclohexane, benzene, for example an ether such as diethyl ether, tetrahydrofuran, dioxane, glycol dimethyl ether, anisole, for example an ester such as ethyl acetate, methyl benzoate, or, for example, a nitrile such as acetonitrile, benzonitrile, or mixtures of such diluents. In a particularly preferred embodiment, a useful isomerization is in the absence of such a liquid diluent.

In addition, it has been found to be advantageous when the isomerization is carried out in a nonoxidative atmosphere, for example under a protective gas atmosphere composed of nitrogen or a noble gas such as argon.

The separation of the mixture which comprises (Z)-2-methyl-2-butenenitrile and 2-methyl-3-butenenitrile may be carried out in any suitable apparatus known to those skilled in the art. Suitable apparatus for the distillation is as described, for example, in: Kirk-Othmer, Encyclopedia of Chemical Technology, 4th Ed., Vol. 8, John Wiley & Sons, New York, 1996, page 334-348, such as sieve tray columns, bubble-cap tray columns, columns having structured packing or random packing, which may also be operated as dividing wall columns. This distillation apparatus is in each case equipped with suitable apparatus for evaporation such as falling-film evaporators, thin-film evaporators, multiphase helical tube evaporators, natural circulation evaporators or forced circulation flash evaporators, and also with apparatus for condensing the vapor stream. The distillation may be carried out in a plurality of, such as 2 or 3, apparatuses, preferably in a single apparatus. The distillation may additionally be effected in one stage in the case of a partial evaporation of the feed stream.

The number of theoretical plates in the distillation column is preferably from 0 to 100, more preferably from 1 to 60, in particular from 10 to 40. The reflux ratio, m(top draw)/–m (reflux to column) is preferably from 0.1 to 500, more preferably from 1 to 200, in particular from 10 to 100. The feed into the distillation column may be in liquid form or gaseous form. The feed may be over the entire height of the column; the feed is preferably at the height of the column which corresponds to from 0 to 90%, in particular from 0 to 50%, of the total number of plates of the column, each counted from the bottom of the column up.

The mixture used in the process according to the invention according to embodiment II preferably has a proportion of 2-methyl-3-butenenitrile in the mixture of from 0.1 to 99% by weight, more preferably from 1 to 99% by weight, in particular from 10 to 90% by weight, based in each case on the sum of the pentenenitrile isomers in the mixture. The proportion of (Z)-2-methyl-2-butenenitrile in this mixture is preferably from 0.1 to 99% by weight, more preferably from 1 to 90% by weight, in particular from 2 to 70% by weight, based in each case on the sum of the pentenenitrile isomers in the mixture.

The process according to the invention according to embodiment II is preferably carried out at a pressure of from 0.001 to 1.0 bar, more preferably from 0.01 to 0.5 bar, in particular from 0.05 to 0.2 bar. The distillation is carried out in such a way that the temperature in the bottom is preferably from 20 to 200° C., more preferably from 30 to 150° C., in particular from 50 to 100° C. The distillation is carried out in such a way that the temperature at the top is preferably from –15 to 200° C., more preferably from 0 to 100° C., in particular from 20 to 50° C. In a particularly preferred embodiment of the process according to the invention, the temperature ranges are maintained both in the bottom and at the top of the distillation column.

At the top of the distillation apparatus, a mixture depleted in 2-methyl-3-butenenitrile compared to the feed stream is obtained. Via the bottom of the distillation apparatus is obtained a mixture depleted in (Z)-2-methyl-2-butenenitrile compared to the feed stream.

In an embodiment III, the process according to the invention relates to the separation of mixtures which comprise cis-2-pentenenitrile and 3-pentenenitrile.

In the hydrocyanation reaction of 3-pentenenitrile to give adiponitrile, cis-2-pentenenitrile is formed and may accumulate in the 3-pentenenitrile circulation stream and is thus preferably removed from the circulation system.

The cis-2-pentenenitrile removed may be isomerized thermally or under catalysis to the 3-pentenenitrile product of value. Mixtures having substantially trans-2-pentenenitrile, trans-3-pentenenitrile and unconverted cis-2-pentenenitrile are obtained. A prerequisite for the insertion of this isomerization step into an integrated process for preparing adiponitrile is that the removal of cis-2-pentenenitrile from this mixture is realizable economically.

According to embodiment III, the present invention thus relates to a process for separating mixtures of isomeric pentenenitriles, wherein the separation is effected distillatively under reduced pressure and the mixture comprises cis-2-pentenenitrile and 3-pentenenitrile. These mixtures stem, for example, from a reaction of 3-pentenenitrile with hydrogen cyanide over a hydrocyanation catalyst. In addition, these mixtures may stem from the thermal or catalyzed isomerization of cis-2-pentenenitrile.

The apparatus demands and the energy requirement for the depletion of cis-2-pentenenitrile from 3-pentenenitrile is high and is determined by the relative volatility α, defined as the ratio of the vapor pressures of these two substances, which is approx. 1.55 at atmospheric pressure, derived from the known standard boiling points of 400.1 K for cis-2-pentenenitrile and 416.8 K for trans-3-pentenenitrile. It has been found in accordance with the invention that the relative volatility of cis-2-pentenenitrile and trans-3-pentenenitrile rises at pressures below atmospheric pressure.

The proportion of cis-2-pentenenitrile in these mixtures is preferably from 0.1 to 99.9% by weight, more preferably from 1 to 99% by weight, in particular from 1 to 90% by weight, based in each case on the sum of the pentenenitrile isomers in the mixture. The proportion of 3-pentenenitrile in the mixture is preferably from 0.1 to 99.9% by weight, more preferably from 1 to 99% by weight, in particular from 2 to 90% by weight, based in each case on the sum of the pentenenitrile isomers in the mixture.

The separation of the mixture which comprises cis-2-pentenenitrile and 3-pentenenitrile may be carried out in any suitable apparatus known to those skilled in the art. Suitable apparatus for the distillation is as described, for example, in: Kirk-Othmer, Encyclopedia of Chemical Technology, 4th Ed., Vol. 8, John Wiley & Sons, New York, 1996, page 334-348, such as sieve tray columns, bubble-cap tray columns, columns having structured packing or random packing, which may also be operated as dividing wall columns. This distillation apparatus is in each case equipped with suitable apparatus for evaporation such as falling-film evaporators, thin-film evaporators, multiphase helical tube evaporators, natural circulation evaporators or forced circulation flash evaporators, and also with apparatus for condensing the vapor stream. The distillation may be carried out in a plurality of, such as 2 or 3, apparatuses, preferably in a single apparatus. The distillation may additionally be effected in one stage in the case of a partial evaporation of the feed stream.

The number of theoretical plates in the distillation column is preferably from 0 to 100, more preferably from 1 to 60, in particular from 10 to 40. The reflux ratio, m(top draw)/−m (reflux to column) is preferably from 0.1 to 500, more preferably from 1 to 200, in particular from 10 to 50. The feed into the distillation column may be in liquid form or gaseous form. The feed may be over the entire height of the column; the feed is preferably at the height of the column which corresponds to from 0 to 90%, in particular from 0 to 50%, of the total number of plates of the column, each counted from the bottom of the column up.

The separation according to embodiment III is preferably effected at a pressure of from 0.001 to 1.0 bar, more preferably from 0.01 to 0.5 bar, in particular from 0.05 to 0.2 bar. The distillation is carried out in such a way that the temperature in the bottom is preferably from 20 to 200° C., more preferably from 30 to 150° C., in particular from 50 to 100° C. The distillation is carried out in such a way that the temperature at the top is preferably from −15 to 200° C., more preferably from 0 to 100° C., in particular from 20 to 50° C. In a particularly preferred procedure of the process according to the invention, the temperature ranges are maintained both in the bottom and at the top of the column.

At the top of the distillation unit is obtained a mixture depleted in 3-pentenenitrile compared to the feed stream. Via the bottom of the distillation unit is obtained a mixture depleted in cis-2-pentenenitrile compared to the feed stream.

In one embodiment IV, the process according to the invention relates to the separation of mixtures which comprise 3-pentenenitrile and (E)-2-methyl-2-butenenitrile.

During the preparation of 3-pentenenitrile, both in the hydrocyanation of 1,3-butadiene and in the isomerization of 2-methyl-3-butenenitrile, a small amount of (E)-2-methyl-2-butenenitrile may be formed as a by-product, in which case the amount of (E)-2-methyl-2-butenenitrile formed is generally found in the product stream together with 3-pentenenitrile. This proportion of (E)-2-methyl-2-butenenitrile accumulates in the existing processes for hydrocyanating 3-pentenenitrile to adiponitrile, as described in DE-A-102 004 004 683, since, in the hydrocyanation, the proportions of unconverted 3-pentenenitrile together with (E)-2-methyl-2-butenenitrile are typically recycled into the reaction, and the proportion of (E)-2-methyl-2-butenenitrile behaves substantially inertly during the reaction and cannot be removed from the system as long as additional measures are not provided for discharging (E)-2-methyl-2-butenenitrile.

The apparatus demands and the energy requirement for depleting (E)-2-methyl-2-butenenitrile from 3-pentenenitrile are high and determined by the relative volatility $\alpha$, defined as the ratio of the vapor pressures of these two substances, which is approx. 1.19 at atmospheric pressure, derived from the known standard boiling points of 410.1 K for (E)-2-methyl-2-butenenitrile and 416.8 K for trans-3-pentenenitrile. It has been found in accordance with the invention that the relative volatility of (E)-2-methyl-2-butenenitrile and 3-pentenenitrile rises at pressures below atmospheric pressure.

In the hydrocyanation process of 3-pentenenitrile to adiponitrile, (E)-2-methyl-2-butenenitrile accordingly accumulates in some cases in the 3-pentenenitrile circulation stream. This circulation stream, as a mixture of pentenenitriles, may be composed, for example, firstly of the proportion of pentenenitriles which are removed directly after the hydrocyanation reaction. Secondly, it is also possible to add to this circulation stream pentenenitriles which remain after the removal of catalyst constituents in the adiponitrile-containing product stream and are removed from this stream for the purpose of recycling, as described in DE-A-102 004 004 683, filed at the same time as the present application.

According to embodiment IV, the process according to the invention is accordingly intended preferentially for mixtures which stem from a reaction of 1,3-butadiene with hydrogen cyanide over a hydrocyanation catalyst, or from an isomerization of 2-methyl-3-butenenitrile or from a reaction of 3-pentenenitrile with hydrogen cyanide over a hydrocyanation catalyst.

In these mixtures, the proportion of 3-pentenenitrile is preferably from 0.1 to 99.9% by weight, more preferably from 1 to 99% by weight, in particular from 10 to 90% by weight, based in each case on the sum of the pentenenitrile isomers in the mixture. The proportion of (E)-2-methyl-2-butenenitrile in the mixture is preferably from 0.1 to 99.9% by weight, more preferably from 0.5 to 99% by weight, in particular from 1 to 50% by weight, based in each case on the sum of the pentenenitrile isomers in the mixture.

The separation of the mixture which comprises 3-pentenenitrile and (E)-2-methyl-2-butenenitrile may be carried out in any suitable apparatus known to those skilled in the art. Suitable apparatus for the distillation is as described, for example, in: Kirk-Othmer, Encyclopedia of Chemical Technology, 4th Ed., Vol. 8, John Wiley & Sons, New York, 1996, page 334-348, such as sieve tray columns, bubble-cap tray columns, columns having structured packing or random packing, which may also be operated as dividing wall columns. This distillation apparatus is in each case equipped with suitable apparatus for evaporation such as falling-film evaporators, thin-film evaporators, multiphase helical tube evaporators, natural circulation evaporators or forced circulation flash evaporators, and also with apparatus for condensing the vapor stream. The distillation may be carried out in a plurality of, such as 2 or 3, apparatuses, preferably in a single apparatus. The distillation may additionally be effected in one stage in the case of a partial evaporation of the feed stream.

The number of theoretical plates in the distillation column is preferably from 0 to 150, more preferably from 1 to 120, in particular from 10 to 60. The reflux ratio, m(top draw)/m (reflux to column) is preferably from 0.1 to 500, more preferably from 1 to 200, in particular from 10 to 100. The feed into the distillation column may be in liquid form or gaseous form. The feed may be at any desired height along the entire height of the column; the feed is preferably at the height of the column which corresponds to from 0 to 90%, in particular from 0 to 50%, of the total number of plates of the column, each counted from the bottom of the column up.

At the top of the distillation unit is obtained a mixture depleted in 3-pentenenitrile compared to the feed stream. Via the bottom of the distillation apparatus is obtained a mixture depleted in (E)-2-methyl-2-butenenitrile compared to the feed stream.

The present invention for separating mixtures of isomeric pentenenitriles leads to the possibility of separating 2-methyl-3-butenenitrile or (E)-2-methyl-2-butenenitrile with in each case 3-pentenenitrile using few separating stages and less energy. In the case of the separation of 2-methyl-3-butenenitrile and (Z)-2-methyl-2-butenenitrile, and also in the case of the separation of (E)-2-methyl-2-butenenitrile and 3-pentenenitrile, the separation or enrichment and depletion is actually made performable in an economic manner with an industrially realizable level of complexity.

The present invention is illustrated in detail with reference to the present working examples.

WORKING EXAMPLES

The following abbreviations are used hereinbelow:
T3PN trans-3-pentenenitrile
C3PN cis-3-pentenenitrile
4PN 4-pentenenitrile
2M3BN 2-methyl-3-butenenitrile
T2PN trans-2-pentenenitrile
C2PN cis-2-pentenenitrile
E2M2BN (E)-2-methyl-2-butenenitrile
Z2M2BN (Z)-2-methyl-2-butenenitrile
VAN valeronitrile
VCH 4-vinylcyclohexene 1. Mixtures Comprising 2-methyl-3-butenenitrile and 3-pentenenitrile The separation is effected in a distillation column having evaporator, total condenser and reflux divider. The distillation column comprises 15 theoretical plates. The reflux ratio m(draw)/m(reflux to column) is 1. The feed is 10 kg/h to stage 10, seen from below, to the distillation column. The draw at the top is 5 kg/h.

The mixture has the following composition:

TABLE 1

| Constituent | Feed % by weight |
| --- | --- |
| T3PN | 51 |
| C3PN | 1 |
| 4PN | 1 |
| 2M3BN | 34 |
| T2PN | 1 |
| C2PN | 1 |
| E2M2BN | 1 |
| Z2M2BN | 8 |

TABLE 1-continued

| Constituent | Feed % by weight |
| --- | --- |
| VAN | 1 |
| VCH | 1 |

TABLE 2

| Example | Pressure (bar) | Temperature bottom ° C. | Temperature top ° C. | 2M3BN bottoms % by weight | 3PN tops % by weight |
| --- | --- | --- | --- | --- | --- |
| 1 | 1.000 | 140 | 126 | 11 | 23 |
| 2 | 0.500 | 117 | 103 | 10 | 22 |
| 3 | 0.200 | 90 | 77 | 8 | 20 |
| 4 | 0.100 | 73 | 59 | 7 | 18 |
| 5 | 0.050 | 58 | 44 | 6 | 17 |
| 6 | 0.020 | 40 | 26 | 4 | 15 |

Examples 1 to 6 show that, at the same reflux ratio and same removal rates, the lower the pressure in the column is set below 1.0 bar, the higher the efficiency with which the separation of 2-methyl-3-butenenitrile and 3-pentenenitrile succeeds: at lower pressure, the residual content of 2-methyl-3-butenenitrile in the bottoms decreases and the residual content of trans-3-pentenenitrile in the tops also decreases.

2. Mixtures Comprising 2-methyl-3-butenenitrile and (Z)-2-methyl-2-butenenitrile The separation is carried out in a distillation column with evaporator, total condenser and reflux divider. The distillation column has 15 theoretical plates. The reflux ratio m(draw)/m (reflux to column) is 50. The feed into the evaporator is at 10 kg/h into the bottom of the column; the draw at the top is at 0.05 kg/h.

TABLE 3

| Constituent | Feed % by weight |
| --- | --- |
| T3PN | 58 |
| C3PN | 1 |
| 4PN | 1 |
| 2M3BN | 21 |
| T2PN | 0 |
| C2PN | 1 |
| E2M2BN | 1 |
| Z2M2BN | 16 |
| VAN | 0 |
| VCH | 1 |

TABLE 4

| Example | Pressure (bar) | Temperature bottom ° C. | Temperature top ° C. | 2M3BN tops % by weight | Z2M2BN tops % by weight |
| --- | --- | --- | --- | --- | --- |
| 7 | 1.000 | 133 | 119 | 23 | 77 |
| 8 | 0.500 | 110 | 97 | 22 | 77 |
| 9 | 0.200 | 84 | 71 | 21 | 78 |
| 10 | 0.100 | 68 | 55 | 20 | 79 |
| 11 | 0.050 | 53 | 40 | 19 | 80 |
| 12 | 0.020 | 38 | 22 | 17 | 82 |

Examples 7 to 12 show that, at the same reflux ratio and same removal rates, the lower the pressure in the column is set, the higher the efficiency with which the separation of 2-methyl-3-butenenitrile and (Z)-2-methyl-2-butenenitrile succeeds: at lower pressure, the residual content of 2-methyl- 3-butenenitrile in the top draw decreases and the content of (Z)-2-methyl-2-butenenitrile in the tops increases.

3. Mixtures Comprising cis-2-pentenenitrile and 3-pentenenitrile

The separation is carried out in a distillation column having evaporator, total condenser and reflux divider. The distillation column has 15 theoretical plates. The reflux ratio m(draw)/m (reflux to column) is 50. The feed is 10 kg/h to stage 10, seen from below, to the distillation column. The draw at the top is at 0.05 kg/h.

TABLE 5

| Constituent | Feed % by weight |
| --- | --- |
| T3PN | 68 |
| C3PN | 3 |
| 4PN | 5 |
| T2PN | 6 |
| C2PN | 9 |
| E2M2BN | 5 |
| Z2M2BN | 0 |
| VAN | 5 |
| VCH | 1 |

TABLE 6

| Example | Pressure (bar) | Temperature bottom °C. | Temperature top °C. | T3PN tops % by weight | C2PN tops % by weight |
| --- | --- | --- | --- | --- | --- |
| 13 | 0.02 | 46 | 29 | 7 | 86 |
| 14 | 0.05 | 61 | 47 | 10 | 82 |
| 15 | 0.1 | 75 | 63 | 13 | 79 |
| 16 | 0.2 | 92 | 80 | 16 | 75 |
| 17 | 0.5 | 118 | 108 | 20 | 69 |
| 18 | 1.00 | 141 | 132 | 24 | 63 |

Examples 13 to 18 show that, at the same reflux ratio and same removal rates, the lower the pressure in the column is set, the higher the efficiency with which the separation of trans-3-pentenenitrile and cis-2-pentenenitrile succeeds: at lower pressure, the residual content of trans-3-pentenenitrile in top draw decreases and the content of cis-2-pentenenitrile to be removed in the tops increases.

4. Mixture Comprising 3-pentenenitrile and (E)-2-methyl-2-butenenitrile

The separation is carried out in a distillation column having evaporator, total condenser and reflux divider. The distillation column has 40 theoretical plates. The reflux ratio m(draw)/m (reflux to column) is 50. The feed is 10 kg/h to stage 5, seen from below, to the distillation column. The draw at the top is at 1.5 kg/h.

TABLE 7

| Constituent | Feed % by weight |
| --- | --- |
| T3PN | 68 |
| C3PN | 3 |
| 4PN | 5 |
| T2PN | 6 |
| C2PN | 9 |
| E2M2BN | 5 |

TABLE 7-continued

| Constituent | Feed % by weight |
| --- | --- |
| Z2M2BN | 0 |
| VAN | 5 |
| VCH | 1 |

TABLE 8

| Example | Pressure (bar) | Temperature bottom °C. | Temperature top °C. | E2M2NB tops % by weight | E2M2BN tops % by weight |
| --- | --- | --- | --- | --- | --- |
| 19 | 0.02 | 55 | 31 | 1.4 | 25.5 |
| 20 | 0.05 | 67 | 49 | 1.5 | 24.7 |
| 21 | 0.1 | 80 | 65 | 1.7 | 24.0 |
| 22 | 0.2 | 95 | 82 | 1.8 | 23.3 |
| 23 | 0.5 | 121 | 109 | 1.9 | 22.6 |
| 24 | 1.00 | 144 | 132 | 1.9 | 22.4 |

Examples 19 to 24 show that, at the same reflux ratio and same removal rates, the lower the pressure in the column is set, the higher the efficiency with which the separation of trans-3-pentenenitrile and (E)-2-methyl-2-butenenitrile succeeds: at lower pressure, the residual content of (E)-2-methyl-2-butenenitrile in the bottom draw stream decreases and increases in the top draw stream.

From Examples 1 to 24, it can be discerned by the converse of the commonly known principles of distillation that, for the achievement of a required specification of the particular pentenenitrile isomers in the bottom and top of the distillation column, when the distillation is performed under reduced pressure, fewer separating stages and/or less energy is needed than would be expected from the consideration of the known standard boiling points.

What is claimed is:

1. A process for separating mixtures of isomeric pentenenitriles, in which at least one isomer is depleted from the mixture, which comprises effecting the separation of the mixtures of isomeric pentenenitriles selected from the group consisting of
   mixtures comprising 2-methyl-3-butenenitrile and 3-pentenenitrile,
   mixtures comprising 2-methyl-3-butenenitrile and (Z)-2-methyl-2-butenenitrile,
   mixtures comprising cis-2-pentenenitrile and 3-pentenenitrile and
   mixtures comprising (E)-2-methyl-2-butenenitrile and 3-pentenenitrile
   by distilling under a pressure of from 0.001 to 1 bar without the addition of a liquid diluent.

2. The process according to claim 1, wherein at least two different isomers are separated.

3. The process according to claim 1, wherein the mixture comprises 2-methyl-3-butenenitrile and 3-pentenenitrile and is produced a reaction of 1,3-butadiene with hydrogen cyanide over a hydrocyanation catalyst.

4. The process according to claim 3, wherein the proportion of 2-methyl-3-butenenitrile in the mixture is from 0.1 to 99.9% by weight, based on the sum of all pentenenitrile isomers in the mixture, and/or the proportion of 3-pentenenitrile in the mixture is from 0.1 to 99.9% by weight, based on the sum of the pentenenitrile isomers in the mixture.

5. The process according to claim 1, wherein the mixture comprises 2-methyl-3-butenenitrile and (Z)-2-methyl-2-butenenitrile and is produced from an isomerization of 2-methyl-3-butenenitrile.

6. The process according to claim 5, wherein the proportion of 2-methyl-3-butenenitrile in the mixture is from 0.1 to 99% by weight, based on the sum of the pentenenitrile isomers in the mixture, and/or the proportion of (Z)-2-methyl-2-butenenitrile in the mixture is from 0.1 to 99% by weight, based on the sum of the pentenenitrile isomers in the mixture.

7. The process according to claim 1, wherein the mixture comprises cis-2-pentenenitrile and 3-pentenenitrile and is produced from a reaction of 3-pentenenitrile with hydrogen cyanide over a hydrocyanation catalyst.

8. The process according to claim 7, wherein the proportion of cis-2-pentenenitrile in the mixture is from 0.1 to 99.9% by weight, based on the sum of pentenenitrile isomers in the mixture, and/or the proportion of 3-pentenenitrile in the mixture is from 0.1 to 99.9% by weight, based on the sum of the pentenenitrile isomers in the mixture.

9. The process according to claim 1, wherein the mixture comprises (E)-2-methyl-2-butenenitrile and 3-pentenenitrile and is produced from a reaction of 1,3-butadiene with hydrogen cyanide over a hydrocyanation catalyst or from the isomerization of 2-methyl-3-butenenitrile or from a reaction of 3-pentenenitrile with hydrogen cyanide over a hydrocyanation catalyst.

10. The process according to claim 9, wherein the proportion of 3-pentenenitrile in the mixture is from 0.1 to 99.9% by weight, based on the sum of the pentenenitrile isomers in the mixture, and/or the proportion of (E)-2-methyl-2-butenenitrile in the mixture is from 0.1 to 99.9% by weight, based on the sum of the pentenenitrile isomers in the mixture.

11. The process according to claim 2, wherein the mixture comprises 2-methyl-3-butenenitrile and 3-pentenenitrile and is produced from a reaction of 1,3-butadiene with hydrogen cyanide over a hydrocyanation catalyst.

12. The process according to claim 2, wherein the mixture comprises 2-methyl-3-butenenitrile and (Z)-2-methyl-2-butenenitrile and is produced from an isomerization of 2-methyl-3-butenenitrile.

13. The process according to claim 2 wherein the mixture comprises cis-2-pentenenitrile and 3-pentenenitrile and is produced from a reaction of 3-pentenenitrile with hydrogen cyanide over a hydrocyanation catalyst.

14. The process according to claim 2, wherein the mixture comprises (E)-2-methyl-2-butenenitrile and 3-pentenenitrile and is produced from a reaction of 1,3-butadiene with hydrogen cyanide over a hydrocyanation catalyst or from the isomerization of 2-methyl-3-butenenitrile or from a reaction of 3-pentenenitrile with hydrogen cyanide over a hydrocyanation catalyst.

* * * * *